United States Patent [19]
Chum et al.

[11] Patent Number: 5,136,111
[45] Date of Patent: Aug. 4, 1992

[54] CONTROLLED CATALYTIC AND THERMAL SEQUENTIAL PYROLYSIS AND HYDROLYSIS OF PHENOLIC RESIN CONTAINING WASTE STREAMS TO SEQUENTIALLY RECOVER MONOMERS AND CHEMICALS

[75] Inventors: Helena L. Chum, Arvada; Robert J. Evans, Lakewood, both of Colo.

[73] Assignee: MRI Ventures, Inc., Kansas City, Mo.

[21] Appl. No.: 710,440

[22] Filed: Jun. 7, 1991

[51] Int. Cl.$^5$ .................. C07C 37/00; C07C 37/52
[52] U.S. Cl. ........................ 568/806; 568/722; 568/724; 568/751; 568/763
[58] Field of Search ............... 568/722, 724, 749, 806, 568/763, 751

[56] References Cited

U.S. PATENT DOCUMENTS

| | | | |
|---|---|---|---|
| 4,131,749 | 12/1978 | Kiedik et al. | 568/806 |
| 4,408,087 | 10/1983 | Li | 568/724 |
| 4,873,376 | 10/1989 | Dujordin et al. | 568/806 |

FOREIGN PATENT DOCUMENTS

| | | | |
|---|---|---|---|
| 463036 | 7/1937 | United Kingdom | 568/806 |
| 880895 | 10/1961 | United Kingdom | 568/806 |

*Primary Examiner*—Werren B. Lone
*Attorney, Agent, or Firm*—Jerome J. Norris

[57] ABSTRACT

A process of using fast pyrolysis in a carrier gas to convert a waste phenolic resin containing feedstreams in a manner such that pyrolysis of said resins and a given high value monomeric constituent occurs prior to pyrolyses of the resins in other monomeric components therein comprising: selecting a first temperature program range to cause pyrolysis of said resin and a given high value monomeric constituent prior to a temperature range that causes pyrolysis of other monomeric components; selecting, if desired, a catalyst and a support and treating said feedstreams with said catalyst to effect acid or basic catalyzed reaction pathways to maximize yield or enhance separation of said high value monomeric constituent in said first temperature program range to utilize reactive gases such as oxygen and steam in the pyrolysis process to drive the production of specific products; differentially heating said feedstreams at a heat rate within the first temperature program range to provide differential pyrolysis for selective recovery of optimum quantity of said high value monomeric constituent prior to pyrolysis of other monomeric components therein; separating said high value monomeric constituent; selecting a second higher temperature program range to cause pyrolysis of a different high value monomeric constituent of said phenolic resins waste and differentially heating said feedstreams at said higher temperature program range to cause pyrolysis of said different high value monomeric constituent; and separating said different high value monomeric constituent.

25 Claims, 4 Drawing Sheets

CONTROLLED CATALYTIC AND THERMAL SEQUENTIAL PYROLYSIS AND HYDROLYSIS OF PHENOLIC RESIN CONTAINING WASTE STREAMS TO SEQUENTIALLY RECOVER MONOMERS AND CHEMICALS

CONTRACTUAL ORIGIN OF THE INVENTION

The U.S. Government has rights in this invention under Contract No. DE-AC02-83H10093 between the United States Department of Energy and the Solar Energy Research Institute, a Division of the Midwest Research Institute.

BACKGROUND OF THE INVENTION

1. Field of the Invention

In general, the invention pertains to a method for controlling the pyrolysis of a complex waste stream of plastics to convert the stream into useful high value monomers and useful chemicals, thereby minimizing disposal requirements for non-biodegradable materials and conserving non-renewable resources. The method uses fast pyrolysis for sequentially converting a plastic waste feed stream having a mixed polymeric composition into high value monomer products by:

using molecular beam spectrometry (MBMS) techniques to characterize the polymeric components of the feed stream and determine process parameter conditions; and differentially heating the feed stream according to a heat rate program using predetermined MBMS data to sequentially obtain optimum quantities of high value monomer products.

If, prior to differential heating, the feed stream catalytically treated to affect thermal reaction pathways, more char is made faster, and the char is a useful chemical in resins and other applications.

The invention achieves heretofore unattained control of a pyrolysis process, as applied to mixed polymeric waste, through greater discovery of the mechanisms of polymer pyrolysis and its utilization, as provided through the use of molecular beam mass spectrometry. Pyrolysis mass spectrometry is used to characterize the major polymers found in the waste mixture, and the MBMS techniques are used on large samples in a manner such that heterogeneous polymeric materials can be characterized in very short time (real time analysis). After characterization, in accordance with the method of the invention, when given a specific waste stream polymer mixture, that mixture is subjected to a controlled heating rate program for maximizing the isolation of desired monomer products, due to the fact that the kinetics of the depolymerization of these polymers have been determined as well as the effects of catalytic (acid/basic) pretreatment.

2. Description of the Prior Art

U.S. Pat. No. 3,546,251 pertains to the recovery of epsilon-caprolactone in good yield from oligomers or polyesters by heating at 210°-320° C. with 0.5 to 5 parts wt. of catalyst (per 100 parts wt. starting material) chosen from KOH, NaOH, alkali earth metal hydroxides, the salts of alkali metals, e.g. Co and Mn and the chlorides and oxides of divalent metals.

U.S. Pat. No. 3,974,206 to Tatsumi et al. discloses a process for obtaining a polymerizable monomer by: contacting a waste of thermoplastic resin with a fluid heat transfer medium; cooling the resulting decomposed product; and subjecting it to distillation. This patent uses not only the molten mixed metal as an inorganic heat transfer medium (mixtures or alloys of zinc, bismuth, tin, antimony, and lead, which are molten at very low temperatures) alone or in the presence of added inorganic salts, such as sodium chloride, etc., by an additional organic heat transfer medium, so that the plastic waste does not just float on the molten metal, and thereby not enjoy the correct temperatures for thermal decomposition. The molten organic medium is a thermoplastic resin, and examples of other waste resins such as atactic polypropylene, other polyolefins, or tar pitch. The added thermoplastic is also partially thermally decomposed into products that end up together with the desired monomers, and therefore, distillation and other procedures have to be used to obtain the purified monomer.

However, Tatsumi et al. provides no means for identifying catalyst and temperature conditions that permit decomposition of a given polymer in the presence of others, without substantial decomposition of the other polymers, in order to make it easier to purify the monomer from the easier to decompose plastic or other high-value chemicals from this polymer.

U.S. Pat. No. 3,901,951 to Nishizaki pertains to a method of treating waste plastics in order to recover useful components derived from at least one monomer selected from aliphatic and aromatic unsaturated hydrocarbons comprising: melting the waste plastic, bringing the melt into contact with a particulate solid heat medium in a fluidized state maintained at a temperature of between 350° to 550° C. to cause pyrolysis of the melt, and collecting and condensing the resultant gaseous product to recover a mixture of liquid hydrocarbons; however, even though one useful monomer is cited, the examples produce mixtures of components, all of which must be collected together and subsequently subjected to purification. No procedure is evidenced or taught for affecting fractionation in the pyrolysis itself by virtue of the catalysts and correct temperature choice.

U.S. Pat. No. 3,494,958 to Mannsfeld et al. is directed to a process for thermal decomposition of polymers such as polymethyl methacrylate using the fluidized bed approach, comprising: taking finely divided polymers of grain size less than 5 mm and windsifting and pyrolysing said polymer grains at a temperature which is at least 100° C. over the depolymerization temperature to produce monomeric products; however, this is a conventional process that exemplifies the utility of thermal processing in general for recovery of specific acrylates. The process of this patent does not acknowledge the need of taking the recovery a step further in the case of more complex mixtures of products, let alone provide a means for doing so.

U.S. Pat. Nos. 4,108,730 and 4,175,211 to Chen et al. relate respectively to treating rubber wastes and plastic wastes by size reducing the wastes, removing metals therefrom, and slurrying the wastes in a petroleum - derived stream heated to 500°-700° F. to dissolve the polymers. The slurry is then fed into a zeolite catalytic cracker operating at 850° F. and up to 3 atmospheres to yield a liquid product, which is a gasoline-type of product (or a mixture of many hydrocarbon products).

While the Chen et al. references exemplify catalytic conversion, it is to a mixture of hydrocarbons boiling in the gasoline range, and not to make specific useful compound(s), which can be isolated by virtue of temperature programming and catalytic conditions.

U.S. Pat. No. 3,829,558 to Banks et al. is directed to a method of disposing of plastic waste polluting the environment comprising: passing the plastic to a reactor, heating the plastic in the presence of a gas to at least the decomposition temperature of the plastic, and recovering decomposition products therefrom. The gas used in the process is a heated inert carrier gas (as the source of heat).

The method of this patent pyrolyses the mixtures of PVC, polystyrene, polyolefins (in equal proportions) at over 600° C., with steam heated at about 1300° F., and makes over 25 products, which were analyzed for, including in the order of decreasing importance, HCl, the main products, butenes, butane, styrene, pentenes, ethylene, ethane, pentane and benzene, among others.

In Banks, no attempt is made to try to direct the reactions despite the fact that some thermodynamic and kinetic data are obtained.

U.S. Pat. No. 3,996,022 to Larsen discloses a process for converting waste solid rubber scrap from vehicle tires into useful liquid, solid and gaseous chemicals comprising: heating at atmospheric pressure a molten acidic halide Lewis salt or mixtures thereof to a temperature from about 300° C. to the respective boiling point of said salt in order to convert the same into a molten state; introducing into said heated molten salt solid waste rubber material for a predetermined time; removing from above the surface of said molten salt the resulting distilled gaseous and liquid products; and removing from the surface of said molten salt at least a portion of the resulting carbonaceous residue formed thereon together with at least a portion of said molten salt to separating means from which is recovered as a solid product, the solid carbonaceous material.

In the Larsen reference, the remainder from the liquid and gaseous fuel products is char. Moreover, these products are fuels and not specific chemicals.

Table 1 provides a summarization of the prior art processes for the thermal decomposition of polymers.

TABLE 1

Thermal decomposition of polymers (adapted from Buekens)

| Process developed by | Reactor type & heating method | Reaction temperature, °C | Plant capacity, tons/day | Feedstock | Products | References |
|---|---|---|---|---|---|---|
| a) Union Carbide | Extruder, followed by annular pyrol. tube, electrically heated | 420–600 | 0.035–0.07 | PE, PP, PS, PVC, PETP, PA, mixes | Waxed | [1] |
| b) Japan Steel Works | Extruder | | | | | [2] |
| c) Japan Gasoline Co. | Tubular reactor, externally heated | | | Dissolved or suspended in recycle-oil | Heavy-oil | [2] |
| d) Prof. Tsutsumi | Tubular reactor, superheated steam as a heat carrier | 500–650 | 1 | PS-foam | | [3] |
| e) Nichimen* | Catalytic fixed by reactor | | | Mixed plast, no char-forming polymers | | [2] |
| f) Toyo Engineering Corp. | Fluidized by catalytic reactor | | 0.5 | Mixed plast, no char-forming polymers | | [2,4] |
| g) Mitsui Shipbuilding & Engineering Co. | Stirred tank reactor, polymer bath | 420–455 | 24–30 | Low mol. w. polymers (PE, APPO | Fuel-oil | [5,4] |
| h) Mitsui Petrochemical Industries Co. (Chiba Works) | | | | | | |
| i) Mitsubishi Heavy Ind. (Mihara Works) | Tank reactor with circulation pump and reflux cooling | 400–500 | 0.7/2.4 | Polyolefins | Naphtha kerosene fuel-oil | [6,4] |
| j) Kawasaki Heavy Ind. (Kakogawa Works) | Polymer bath, formed by PE and PS | 400–450 | 5 | Mixed plast. PE + PS content 55% | Gas-oil HCL. | [2,4] |
| k) Ruhrchemie AG, Oberhausen | Stirred tank reactor, salt bath | 380–450 | 1.2 | PE | Oil, wax | [7] |
| l) Japan Gasoline Co. | Fluidized bed | 450 | 0.2 | PS-waste | | [8] FIG. 16 See [8] |
| m) Prof. Sinn, Univ. of Hamburg Prog. Kaminsky | Fluidized bed | 640–840 | Laboratory scale | PE, PS, PVC tyre rubber | Aromatic hydro-carbons & fuel oil | |
| n) Sanyo Electric Co. | Molten salt bath | 600–800 | Laboratory scale | | Monomer | [8,3,4] |
| | Tubular reactor with a screw for carbon removal, dielectric heating | 260 (PVC), followed by 500–550 | 0.3 (pilot) 3 (Gifu) 5 (Kusatsu) | Foam PS, mixed plast. (select, collect.) asphalt 6% S | Fuel-oil HCL | |
| o) Sumitomo Shipbuild. & Machinery Co. (Hiratsuka Lab.) | Fluidized bed, partial oxidation | 450–470 600 (28) | 3–5 | Mixed plastics incl. PVC | Heavy oil HCL | [8,4] HCL |
| p) Government Industrial Research Institute | Fluidized bed, partial oxidation | 400–510 550 | Bed diameter: 3.5/ 15/30/50 & 120 cm | PS-chips | Monomer and dimer Gasific. prod. | [9] |
| q) Nippon Zeon, Japan Gasoline Co. (Tokuyama) | Fluidized bed, partial oxidation | 350–600 (400–500 mostly) | 24 pre-commercial plant | Sheared tyres | Gas, oil, char | [10] |
| r) Kobe Steel | Externally heated, rotary kiln | 600–800 | 5 (pilot) | Crushed tyres | Gas, oil, char | [8,11] |
| s) Bureau of Mines/ Firestone | Electrically heated retort | 500/900 | Laboratory scale | Tyre cuttings | Gas, oil, char | [12] |
| t) Hydrocarbon Research Inc. | Autoclave | 350–450 | | Tyres | | [8] |
| u) Zeplichal | Conveyor band, vacuum | | | Tyres | | [8] |

TABLE 1-continued

Thermal decomposition of polymers (adapted from Buckens)

| Process developed by | Reactor type & heating method | Reaction temperature, °C. | Plant capacity, tons/day | Feedstock | Products | References |
|---|---|---|---|---|---|---|
| v) Herbold, W. Germany | | | | Tyres | | [13] |

References
[1] J. E. Potts, Reclamation of plastic waste by pyrolysis, Am. Chem. Soc., Div. Water, Air, and Waste Chemistry, Chicago, p. 229, 13-18 September (1970).
[2] M. Endo, Techniques for pyrolysing plastics waste, Japan Plastics Q. 29, October (1973).
[3] S. Tsutsumi, Thermal and steam cracking of waste plastics, Conference Papers of the First International Conference, Conversion of refuse to energy, Montreux (Switzerland), 4 November (1975) p. 567.
[4] Staff Writers, Trends in development of plastic waste disposal techniques, Cem. Econ. Engng. Rev. 4, (10), 29 (1972).
[5] Y. Kitaoka and H. Sueyoshi, Conversion of waste polymer to fuel oil, Conference Papers of the First International Conference, Conversion of refuse to energy, Montreux (Switzerland), 4 November (1975) p. 555.
[6] K. Matsumoto, S. Kuritsu and T. Oyamoto, Development of process of fuel recovery by thermal decomposition of waste plastics, Conference Papers of the First International Conference, Conversion of refuse to energy, Montreux (Switzerland) 4 November (1975) p. 338.
[7] S. Speth, Aufarbeitung von Polyathylen-Ruckstanden zu Niedermolekularen Destillaten, Chemie Ing. Tech. 45, (8), 526 (1973).
[8] W. Kaminsky, J. Menzel and H. Sinn, Recycling of plastics, Conservation and Recycling, 1, (1), 91 (1976).
[9] S. Mitsui, H. Nishizaki and K. Yoshida, Communication at ACHEMA, Frankfurt (1976).
[10] Y. Saeki and G. Suzuki, Fluidized thermal cracking process for waste tire, Rubber Age, February (1976).
[11] A. Takamura, K. Inque and T. Sakai, Resources recovery by pyrolysis of waste tyres, Conference Papers of the First International Conference, Conversion of refuse to energy, Montreux (Switzerland), 4 November (1975) p. 532.
[12] J. A. Beckman, D. J. Bennett, A. G. Altenau and J. R. Laman, Yields and analyses of the products from the destructive distillation of scrap tyres, Conference Papers of the First International Conference, Conversion of refuse to energy, Montreux (Switzerland), 4 November (1975) p. 195.
[13] H. W. Schnecko, Zur Pyrolyse von Altreifen, Chem. Ing. Tech. 48 (5), 443 (1976).

SUMMARY OF THE INVENTION

One object of the present invention is to provide a method for controlling the pyrolysis of a complex waste stream of phenolic resins to convert the stream into useful high value monomers, by identifying catalyst and temperature conditions that permit decomposition of a given polymer in the presence of others, without substantial decomposition of the other polymers, in order to make it easier to purify the monomer from the easier to decompose plastic.

A further object of the invention is to provide a method for controlling the pyrolysis of a complex waste stream of phenolic resins by affecting fractionation in the pyrolysis itself by virtue of correct choice of conditions including temperature and catalysts if desired.

A yet further object of the invention is to provide a method of using fast pyrolysis to convert a phenolic waste feed stream having a mixed polymeric composition into high value monomers products by:

using molecular beam mass spectrometry (MBMS) to characterize the components of the feed steam; catalytically treating the feed stream to affect acid thermal reaction pathways, if desired; and differentially heating the feed stream according to a heat rate program using predetermined MBMS data to provide optimum quantities of said high value monomer products.

A still further object of the invention is to provide a method of using fast pyrolysis to convert waste from plastics manufacture of phenolic resins alone or in combination with other resins by using the molecular beam mass spectrometry, catalytic treatment and differential heating mentioned above.

Another object of the invention is to provide a method of using fast pyrolysis to convert waste consumer products manufacture such as phenolics or mixed plastic waste from the plants in which these phenolics are converted into consumer products, in which case, the number of components present in the waste increases as does the complexity of the stream, by using the molecular beam mass spectrometry, catalytic treatment, if desired, and differential heating mentioned above.

Still another object of the invention is to provide a method of using fast pyrolysis to convert wastes from phenolics manufacture, consumer product manufacture and the consumption of products such as source separated mixed phenolics (or individually sorted types); mixed phenolics from manufacture of phenolic resins and processing of these and other phenol-derived plastics; and mixed phenolics from durable goods (e.g., electrical appliances and automobiles) after their useful life, by using molecular beam mass spectrometry, catalytic treatment and differential heating mentioned above.

BRIEF DESCRIPTION OF THE DRAWINGS

The accompanying drawings which are incorporated in and form a part of the specification will illustrate preferred embodiments of the present invention, and together with the description, will serve to explain the principles of the invention.

FIG. 2A shows the relative abundance in arbitrary units at various temperatures.

FIG. 2B shows mass spectral data analysis for the solid line curve component of spectrum 1 in FIG. 2A.

FIG. 2C shows mass spectral analysis for the dotted line curve component of spectrum 2 in FIG. 2A.

FIGS. 3 shows the results of temperature programmed pyrolysis of a phenolic novolac resin showing the effect of a low temperature treatment in oxygen and without oxygen on the product distribution from subsequent high temperature flash-pyrolysis.

FIGS. 3A–3C show the results of a novolac sample pyrolyzed without oxygen, wherein FIG. 3A shows the product distributions over several temperature ranges, FIG. 3B shows the integrated product spectra taken over the interval of product evolution described by the curve for m/z 94 (phenol), and FIG. 3C shows the novolac sample pyrolyzed without oxygen and the product distribution typical of novolac pyrolysis.

DETAILED DESCRIPTION OF THE INVENTION

Figure 1A:
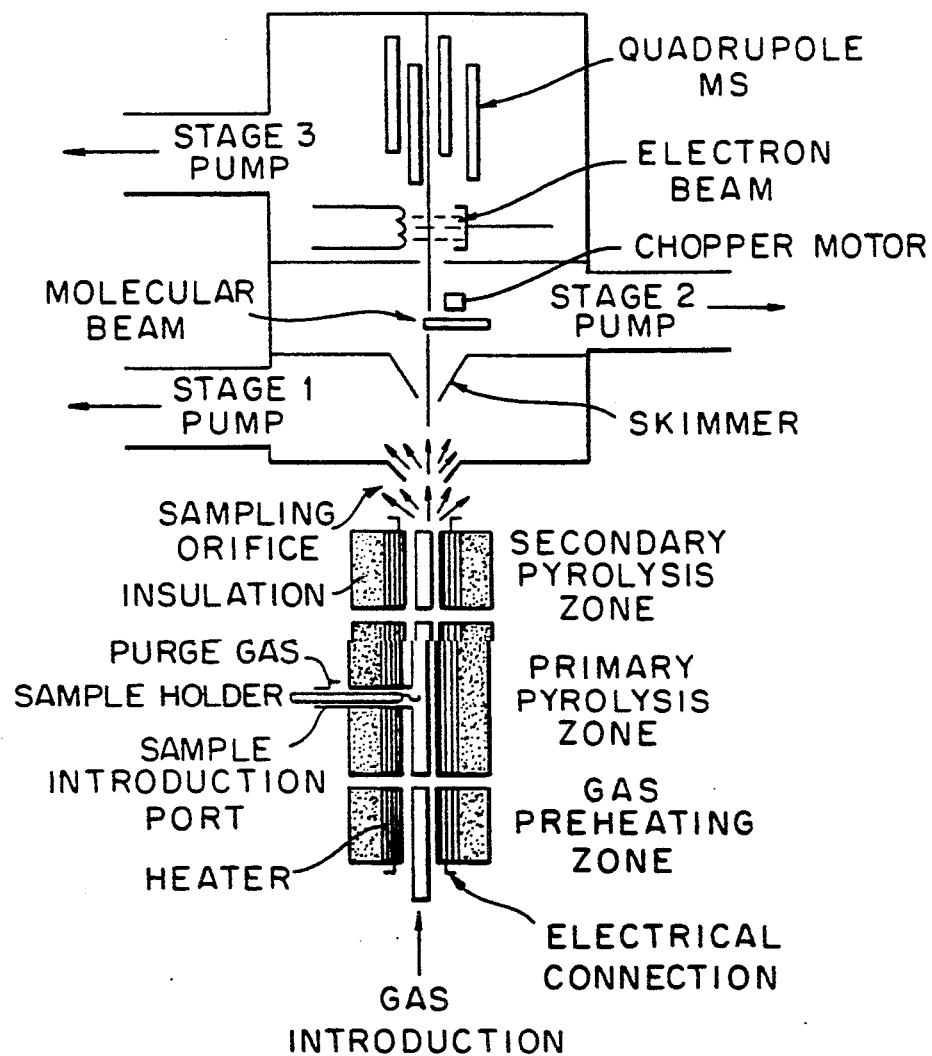
FIG. 1A is a schematic of the molecular beam mass spectrometer coupled to a tubular pyrolysis reactor used for screening experiments.

Through the use of the invention, it has been generally discovered that, by the novel use of molecular beam mass spectrometry techniques applied to pyrolysis, a rapid detection of a wide range of polymers or plastics decomposition products can be determined in real time in order to provide unique observations of the chemistry of pyrolysis. The observations or data of the analytical method of MBMS is then combined with other systems of data analysis in order to characterize complex reaction products and determine optimum levels of process parameters.

The results of MBMS applied to pyrolysis indicate that there are basically three methods of controlling the pyrolysis of phenolic resin containing synthetic polymers: (1) the utilization of the differential effect of temperature on the pyrolysis of different components and (2) the feasibility of performing acid- and base-catalyzed reactions in the pyrolysis environment to guide product or monomer distribution and (3) the use of coreactants to alter products such as steam or oxygen.

By the use of the invention process, MBMS techniques can now be used to rapidly study the pyrolysis of the major components of industry waste stream to determine optimum methods for temperature-programmed, differential pyrolysis for selective product recovery.

Another aspect of the invention is that product composition can be controlled by the use of catalysts for the control of reaction products from pyrolysis and from hydrolysis reactions in the same reaction environment.

Despite the complex nature of the waste stream, it is apparent that evidence exists to enable the discovery and exploitation of the chemical pathways, and that it is possible to attain a significant level of time-dependent product selectivity through reaction control of the effect of these two process variables; namely, differential heating and catalytic pretreatment.

It is well known that the disposal of the residues, wastes, or scraps of plastic materials poses serious environmental problems.

Examples of these plastics include thermoset phenolic resins. An example of these plastics is novolacs which are a large source of materials. Wastes of these materials are also produced in the manufacturing plants.

These materials, amongst others, are widely used in adhesives, molding compositions, phenolic beam insultation, and many other applications.

These materials are very durable, and their environmental disposal is done with difficulty because of their permanence in the environment. Their disposal in mass burning facilities confront all emissions environmental problems and this makes siting of these plants near urban and rural communities very difficult.

On the other hand, landfill is a poor alternative solution as the availability of land for such purposes becomes scarce and concerns over leachates and air emissions (methane) from these landfills poses serious doubts as to whether these traditional methods are good solutions to waste disposal.

The invention is premised on the recognition of the pyrolytic processes as applied to mixtures, in such a way, that by simultaneously programming the temperature (analytical language), or in multiple sequential stages of engineering reactors at different temperatures (applied language) by discovering the appropriate type of catalysts and reaction conditions, the mixture can generate high yields of specific monomeric or high value products from individual components of the mixed plastic stream in a sequential way, without the need to pre-sort the various plastic components.

In other words, substantial advantages of the invention are obtained by trading off the pre-sorting costs with those for the isolation of pyrolysis products and their purification from each individual reactor/condenser in the process.

The process of the invention is versatile and can be applied to a wide variety of plastic streams. Each stream requires the selection of specific conditions of temperature sequence, catalyst, and reaction conditions, such that the highest yields of single (or few) products can be obtained at each pyrolysis stage.

An example in the area of waste from consumer product manufacture is novolacs, which yields phenol, cresols, di-methyl phenol and bis-phenols.

One example of waste from consumer product manufacture subject to the invention process are manufacturing wastes. The major use of these technologies is for the recovery of value or monomers from the blends, which would be more difficult to recycle in other ways. These wastes would be suitable for conversion in the present process.

Sequential processes consisting of initial operation at low temperature with (or without) catalysts (e.g. base or other catalysts) may be used to recover key monomers and low boiling solvents. The initial pyrolysis can be followed by high temperature in the presence of steam. The types of compounds and their proportions can be tailored by the operation conditions. Support for the feasibility of such processes comes from the analytical area of pyrolysis as a method of determination of composition of composites, for instance, based on styrene copolymers, ABS-polycarbonate blends, as taught by V. M. Ryabikova, A. N. Zigel, G. S. Popova, Vysokomol. Soedin., Ser. A, vol. 32, number 4, pp. 882-7 (199), and various references mentioned above.

Other examples are phenolic resins, which produce phenol and cresols upon pyrolysis, in addition to chars. Other thermosetting resins can also be used to yield some volatile products, but mostly char, which can be used for process heat.

The invention will henceforth describe how to utilize detailed knowledge of the pyrolytic process in the presence or absence of catalysts, as a function of temperature, and the presence of reactive gases, to obtain high yields of monomers or valuable high value chemicals from mixtures of plastics in a sequential manner. The conditions need to be found experimentally, since it is not obvious which sets of catalysts, temperature program, and reactive gases and conditions will favor specific pathways for the optimization of one specific thermal pathway to one (or few) products, when several are available and the multicomponent mixture offers an increased number of thermal degradation pathways. In order to accomplish this, pyrolysis is carried out in the presence of appropriate catalysts appropriate to temperature conditions, and reactive gases to produce specific compounds; the temperature is then raised and a second product can be obtained; finally any additional polymers which are not substantially cleaved can be burned to process heat, or upgraded into a monomer known in the prior art, such that by addition of catalysts, such as metals on activated carbons, these compounds will be transformed. The fate of the additional polymers fraction will depend on the specific location of the plant and of the need to obtain heat/electricity or chemicals to make a cost-effective operating plant.

Many types of reactors can be applied to the present art, from fluidized beds to batch reactors, fed by extruders at moderate temperatures or other methods (dropping the plastic into the sand bath). Molten salts can also be used. The prior art contains substantial examples of the ability to operate and produce mixtures of products from pyrolysis of plastic wastes. Specific two-stage systems for pyrolysis at two different temperatures are given but the goal was a fuel product.

The present invention makes the plastics recycling processes more cost-effective because it makes it possible to produce higher value products by tailoring the operation of the process.

DETAILED DESCRIPTION OF THE PREFERRED EMBODIMENTS

Figure 1B:
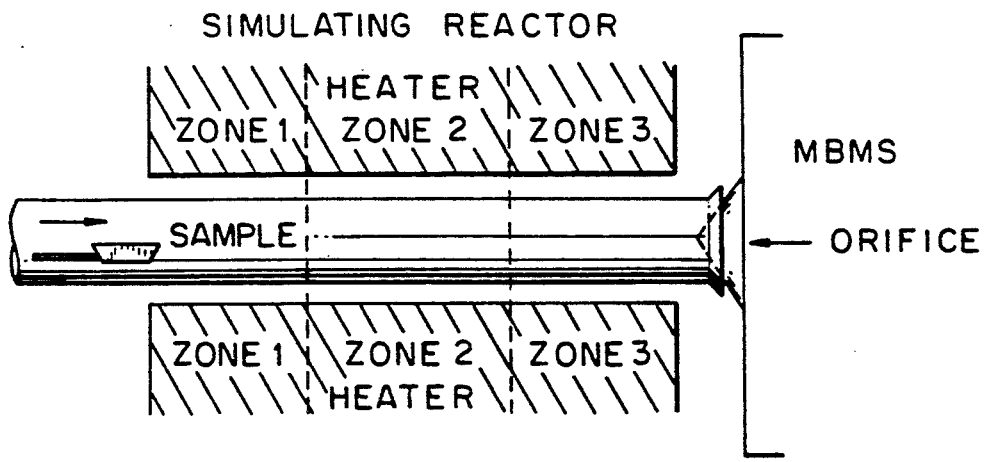
FIG. 1B is a schematic of the slide-wire pyrolysis reactor used to subject samples to batch, temperature-programmed pyrolysis.

The type of equipment used is a 1) small-scale (5-50 mg sample) tubular reactor experiments that use pulse samples and utilize a mass spectrometer for real time product analysis and allow the determination of reaction conditions; helium is used as a carrier gas for these types of experiments. A simplified schematic of the molecular beam mass spectrometer (MBMS) coupled with a tubular pyrolysis reactor the stirred autoclave is shown in FIG. 1A. The MBMS was used with a slide wire reactor shown in FIG. 1B to accomplish temperature-programmed pyrolysis in a pulse mode operation.

The following examples show the components of the process and how it can be applied to specific, mixed wastes with the production of high value materials by control of heating rate, co-reactants, and condensed-phase catalysts.

The results show that temperature-programming, catalysts and co-reactant gases can be judiciously selected to deal with complex mixtures of plastics to recover monomer value in addition to energy value.

EXAMPLE 1

RECOVERY OF PHENOL/CRESOLS AND CHAR FROM PHENOLIC RESINS (NOVOLACS), ALONE OR IN COMBINATION WITH OTHER RESINS

Figure 2A:
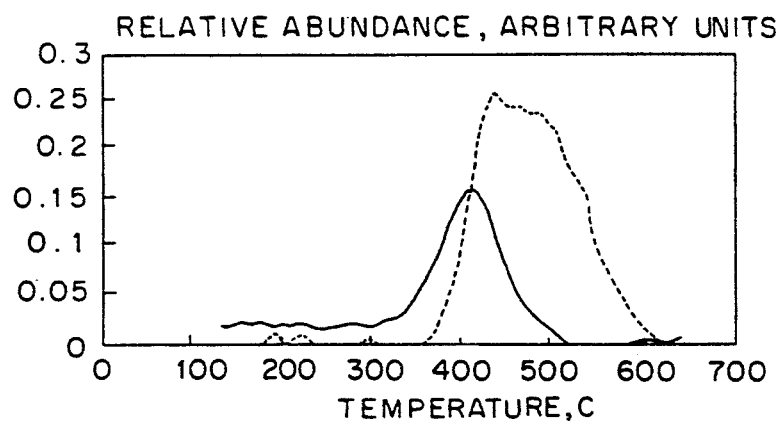
FIG. 2A–C shows the results of temperature-programmed pyrolysis of a phenolic novolac resin made from phenol and wood-derived phenolic mixtures where the evolution curve of the two main groups of peaks, as determined by factor analysis of the time-resolved mass spectra and the reconstructed mass spectra of the two groups of peaks.
Figure 2B:
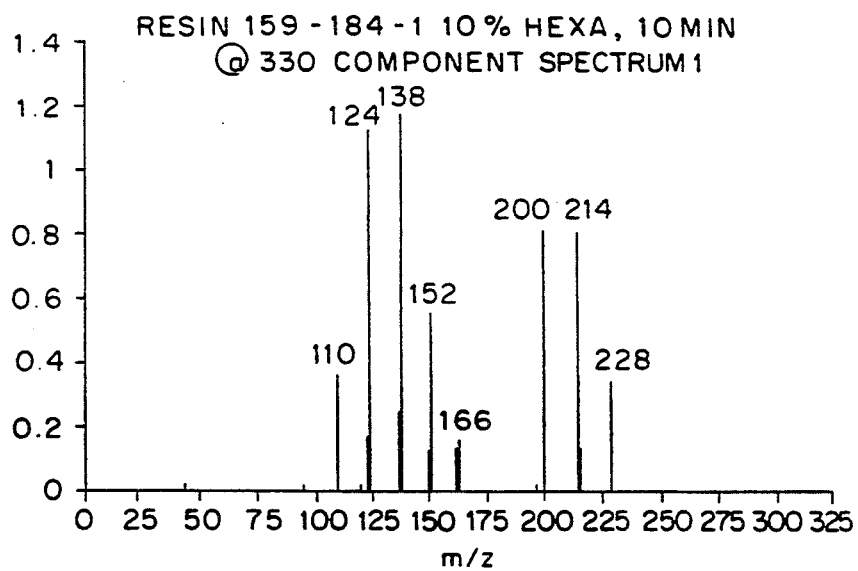
Figure 2C:
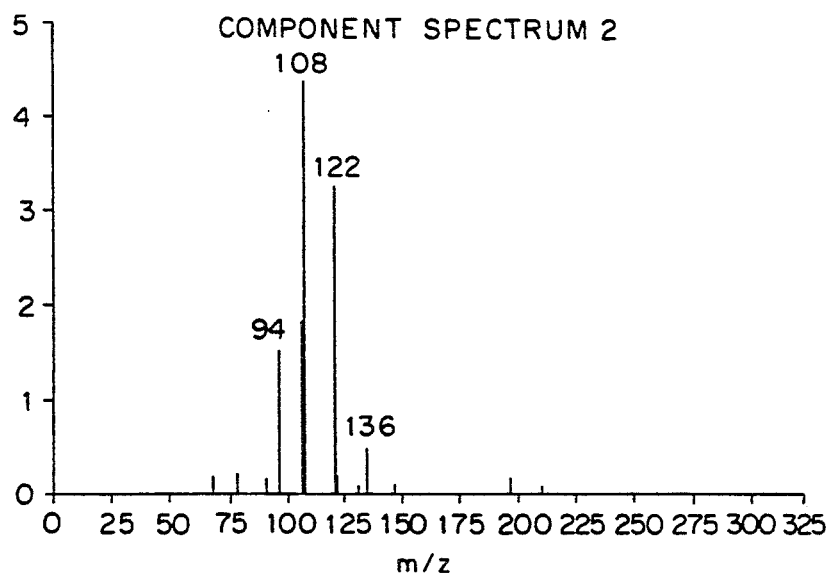
Figure 3A:
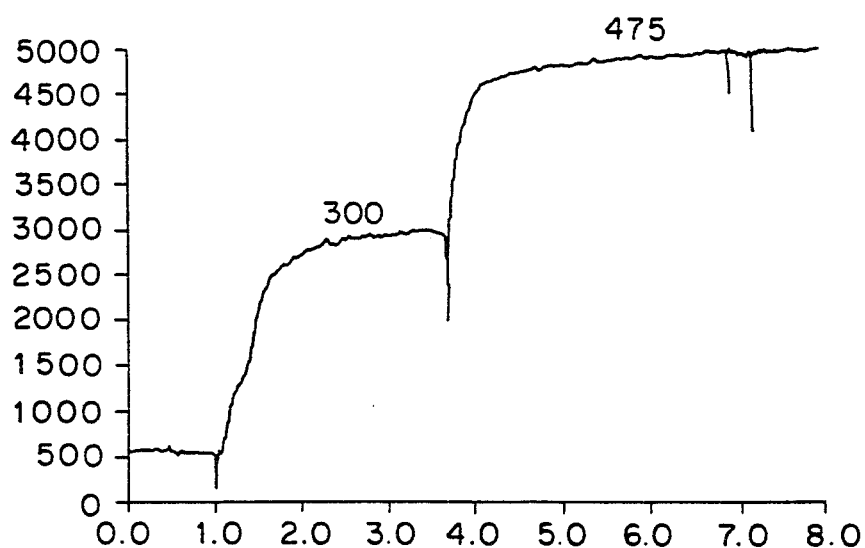
Figure 3B:
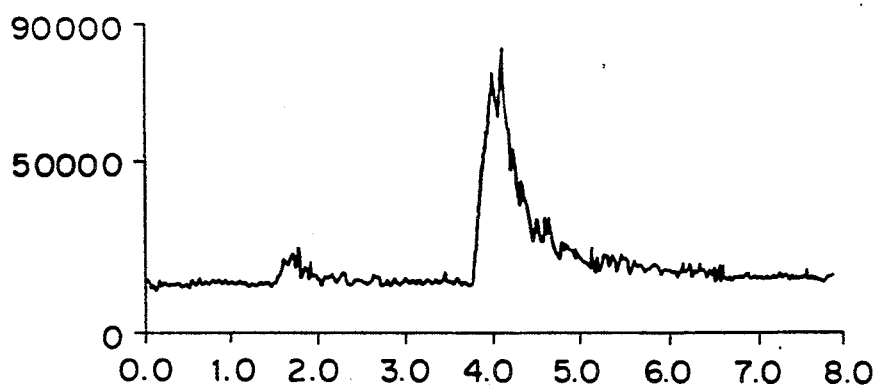
Figure 3C:
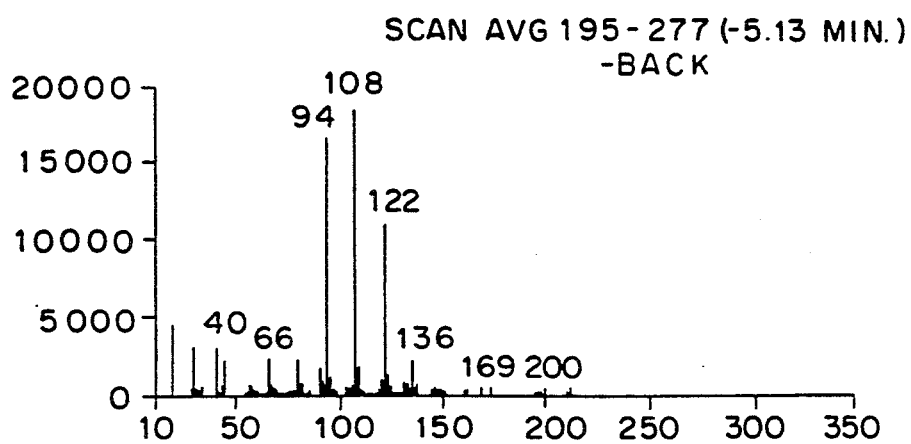
Figure 3D:
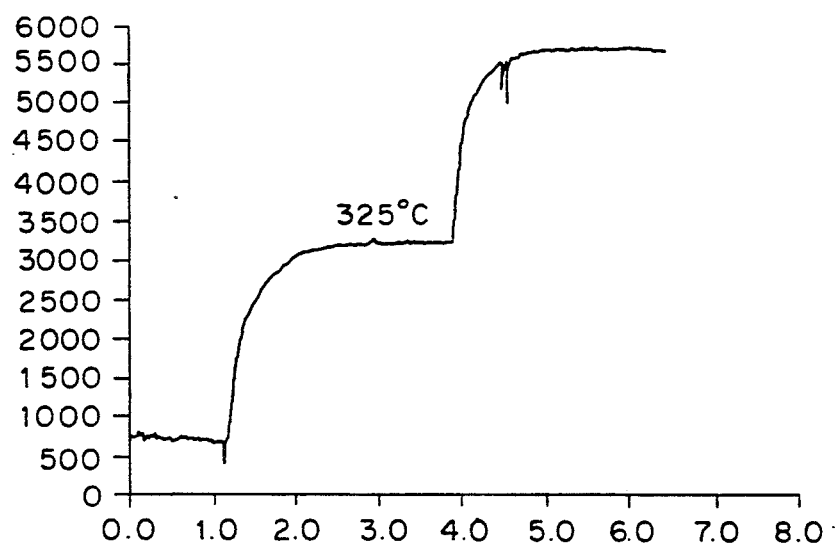
FIG. 3D shows temperature range for pyrolyzed novolac samples in which the carrier gas contains 20% oxygen.
Figure 3E:
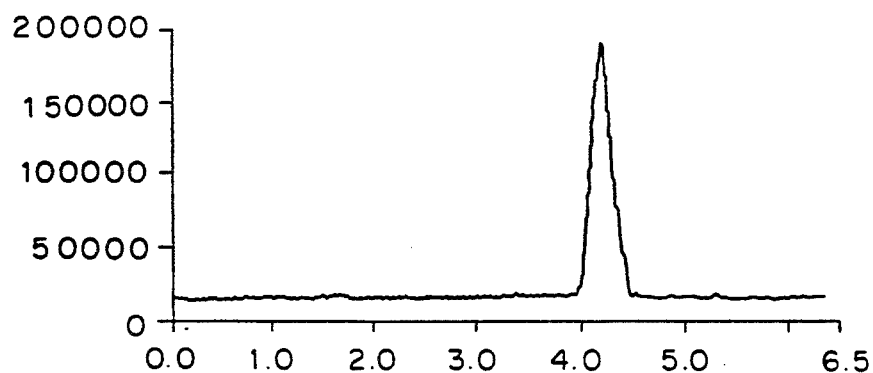
FIG. 3E shows the integrated product spectra taken over the interval of product evolution as described by the curve for m/z 94 (phenol) when the carrier gas is 20% oxygen and FIG. 3F shows the integrated product spectrum for a change in product distribution for pyrolyzed novolac samples in which the carrier gas is 20% oxygen.
Figure 3F:
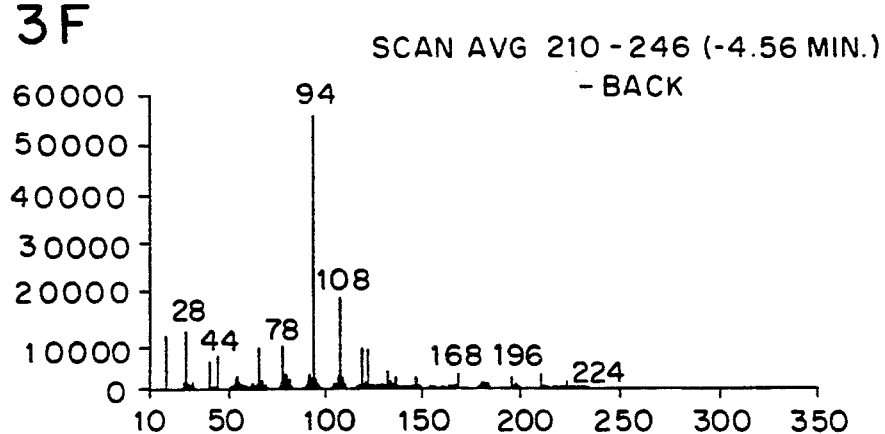

When phenol/formaldehyde resins are pyrolyzed, they produce a series of methyl-substituted phenolic monomers and dimers in about 50% yield. In this example it is shown that product selectivity can be controlled by control of the heating rate. A novolac was made from phenol, P/N oil, and formaldehyde (1:1:0.3), catalyzed with $H_2SO_4$ and cured with 10% Hexa at 330° C. for 10 minutes. The P/N oil is a phenolic material that was derived from the pyrolysis of pine and separated from the crude oil by solvent extraction (H. L. Chum and S. Black, U.S. Pat. No. 4,942,269). This patent is incorporated by reference in its entirety, and teaches that the P/N oil can be substituted in novolac up to 50% without degradation of performance. This novolac was pyrolyzed at a heating rate of 40° C./min to a final temperature of 700° C. Two groups of compounds can be distinguished by time-resolved mass spectral data analysis. These results are shown in FIG. 2. A first group of compounds appear at 400° C. and is composed of two homologous series: one based on dihydroxybenzene and one on the dimer bis-phenol. A second group has a maximum at 450° C. and is composed of a homologous series based on phenol and its methyl derivatives. The ability to control the relative amounts of these two groups allow the recovery of valuable starting materials that can be substituted for phenol in novolac formulations in much the same way as the P/N oil is substituted.

This technology applies to novolacs prepared with phenol/formaldehyde alone.

This is demonstrated in FIG. 3 where a novolac sample was pyrolyzed with and without the presence of oxygen in the carrier gas. The slide-wire reactor (FIG. 1A) was used to subject the samples to batch, temperature-programmed pyrolysis. A low temperature stage was used to partially react the material in the presence of oxygen and increase the overall yield of phenolics. In FIGS. 3A-C the material was reacted without oxygen and a product distribution typical of novolac pyrolysis was obtained as shown in FIG. 3C, which is the integrated product spectra taken over the interval of product evolution as described by the curve for m/z 94 (phenol) shown in FIG. 3B. Compare FIG. 3C with FIG. 2C in the pyrolysis of P/N containing novolacs. The low temperature phase of 2 minutes at 300° C. has no effect on product distribution without oxygen present. In FIGS. 3D-F, the carrier gas is 20% oxygen and the major difference, as shown by the integrated product spectrum in FIG. 3F, is a change in product distribution. A low temperature pretreatment of the sample in flowing oxygen and with steam and catalyst present will increase the overall yield as well as favor the formation of phenol over other substituted phenolics. Optimization of conditions leads to a time and temperature sequence where partial oxidation occurs and carbon bond cross-linking is minimized, leading to higher yields when the flash pyrolysis step is performed at the higher temperature.

This technology also applies with partially substituted phenol with lignins from the fast pyrolysis of biomass as well as resole resins. The residue is a char, which is present at a level of 30–40%, and this leads to usable products in resin making or other applications.

There is no similarity between the prior art and the present invention.

The prior art is based on hydrolysis and solvolysis of pure polymer streams. These involve the presence of a solvent, a catalyst, and high-temperature and pressures, as distinguished from the present invention.

Although there is substantial literature of the pyrolysis of these plastics as an analytical tool for the identification of these polymers in mixtures, as well as some work dealing with the mixtures of plastics addressing the formation of liquid fuels or a variety of products, the specific conditions for the formation of essentially simple pyrolysis products in high yields has not yet been identified in the prior art except for two classes of polymers known to thermally decompose into monomers, namely polycrylates and polytetrafluoroethylases. All other plastics have been known to decompose into multiple products through multiple pathways.

While the foregoing description and illustration of the invention has been shown in detail with reference to preferred embodiments, it is to be understood that the foregoing are exemplary only, and that many changes in the compositions can be made without departing from the spirit and scope of the invention, which is defined by the attached claims.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not limitation.

What is claimed is:

1. A process of using fast pyrolysis in a carrier gas to convert a waste phenolic resin containing feed stream in a manner such that pyrolysis of said resin and a given high value monomeric constituent occurs prior to pyrolysis of said resin and other monomeric components therein comprising:
    a) selecting a first temperature program range of between about 250° to 300° C. to cause pyrolysis of said resin and a given high value monomeric constituent prior to a temperature range that causes pyrolysis of other monomeric components;
    b) differentially heating said feed stream at a heat rate within the first temperature program range to provide differential pyrolysis for selective recovery of optimum quantities of said high value monomeric constituent prior to pyrolysis of other monomeric components therein;
    c) separating said high value monomer constituent;

d) selecting a second higher temperature program range between about 350° to 700° C. to cause pyrolysis of a different high value monomeric constituent of said waste phenolic resin and differentially heating said feed stream at said higher temperature program range to cause pyrolysis of said different high value monomeric constituent; and e) separating said different high value monomeric constituent.

2. The process of claim 1, wherein said phenolic resin comprises a phenol/formaldehyde novolac resin; said high value monomeric constituent is phenol; and said different high value monomeric constituent is selected from substituted phenols.

3. The process of claim 2, wherein the feed stream is manufacturing waste.

4. The process of claim 2, wherein no catalysts and no catalysts supports are used.

5. The process of claim 4, wherein said carrier gas is selected from inert gases, $CO_2$ and process recycle gases.

6. The process of claim 5, wherein said first temperature range program is used to partially react said resin in the presence of oxygen to increase the yield of specific phenolics.

7. The process of claim 6, wherein oxygen is present in an amount of 20% by volume of said carrier gas.

8. The process of claim 1, wherein said phenolic resin comprises a novolac made from phenol, P/N oil and formaldehyde; said high value monomeric constituent is selected from the group consisting of dihydroxy benzene and bis-phenol dimer or mixtures thereof; and said different high value monomeric constituent is selected from phenol, its methyl derivatives or mixtures thereof.

9. The process of claim 8, wherein said feed stream is manufacturing waste.

10. The process of claim 8, except that said first temperature range program is between about 350° to about 400° C., and except that said second higher range temperature program is between about 400° to about 450° C.

11. The process of claim 10, wherein said second higher range temperature program is pyrolyzed at a heating rate of 40° C./min and extended while being pyrolyzed to a final temperature of about 700° C.

12. The process of claim 1, wherein said phenolic resin comprises a novolac made from phenol, P/N oil and formaldehyde; said high value monomeric constituent is selected from the group consisting of dihydroxy benzene and bis-phenol dimer or mixtures thereof; and said different high value monomeric constituent is selected from phenol, its methyl derivatives or mixtures thereof.

13. The process of claim 12, except that said first temperature range program is between about 350° to about 400° C. and said second higher range temperature program is between about 400° to about 450° C.

14. The process of claim 13, wherein said second higher range temperature program is pyrolyzed at a heating rate of 40° C./min and extended while being pyrolyzed to a final temperature of about 700° C.

15. The process of claim 1, wherein said phenolic resin is a phenol/formaldehyde resin in which phenol is partially substituted with a lignin.

16. The process of claim 15, wherein said lignin is from fast pyrolysis of biomass.

17. The process of claim 1, wherein said phenolic resin is a resole resin.

18. The process of claim 1, wherein said resole resin is one in which phenol is partially substituted with a P/N oil.

19. The process of claim 2, wherein char is a residue.
20. The process of claim 8, wherein char is a residue.
21. The process of claim 12, wherein char is a residue.
22. The process of claim 15, wherein char is a residue.
23. The process of claim 16, wherein char is a residue.
24. The process of claim 17, wherein char is a residue.
25. The process of claim 18, wherein char is a residue.

* * * * *